(12) United States Patent
Coale (10) Patent No.: US 9,060,826 B2
(45) Date of Patent: Jun. 23, 2015

(54) METHOD AND APPARATUS FOR DELIVERING BONE CEMENT

(75) Inventor: Bradford J. Coale, Vernon, NJ (US)

(73) Assignee: EBI, LLC, Parsippany, NJ (US)

( * ) Notice: Subject to any disclaimer, the term of this patent is extended or adjusted under 35 U.S.C. 154(b) by 78 days.

(21) Appl. No.: 12/746,113

(22) PCT Filed: Apr. 3, 2009

(86) PCT No.: PCT/US2009/039412
§ 371 (c)(1),
(2), (4) Date: Jun. 3, 2010

(87) PCT Pub. No.: WO2010/114557
PCT Pub. Date: Oct. 7, 2010

(65) Prior Publication Data
US 2012/0029521 A1    Feb. 2, 2012

(51) Int. Cl.
*A61B 17/58* (2006.01)
*A61B 17/60* (2006.01)
*A61F 2/00* (2006.01)
*A61B 17/88* (2006.01)

(52) U.S. Cl.
CPC ......... *A61B 17/8827* (2013.01); *A61B 17/8822* (2013.01)

(58) Field of Classification Search
CPC ............. A61B 17/00; A61B 17/8802; A61B 2017/8813; A61B 17/8833; A61M 5/31511; A61M 5/5066; A61M 5/1782; A61M 5/31596; A61M 2005/31598; A61M 2005/1787
USPC ........... 606/92–94, 191; 222/319, 383.3, 385, 222/383.1, 386, 390, 391, 372, 373; 604/57, 59, 248, 246, 121, 218–238
See application file for complete search history.

(56) References Cited

U.S. PATENT DOCUMENTS

| 212,046 | A | * | 2/1879 | Palmer | 604/183 |
| 938,544 | A | | 11/1909 | Ball | |

(Continued)

FOREIGN PATENT DOCUMENTS

| EP | 1400213 A1 | 3/2004 |
| FR | 2829690 A1 | 3/2003 |
| GB | 2338428 A | 12/1999 |

OTHER PUBLICATIONS

Supplementary European Search Report for related EP Application No. 09842824.6, dated Sep. 26, 2013.

*Primary Examiner* — David Bates
*Assistant Examiner* — Samuel Hanna
(74) *Attorney, Agent, or Firm* — Harness, Dickey (57) ABSTRACT

The present teachings provide one or more surgical instruments for repairing damaged tissue, such as in the case of a vertebral compression fracture. The present teachings can provide a bone cement system. The system can include a housing, which can define at least a throughbore that can extend from a proximal end to a distal end of the housing. The system can also include a dispenser housing received in the throughbore of the housing that is adapted to receive a bone cement. The system can include a plunger, which can be releasably coupled to the proximal end of the housing and received into the dispenser housing so that movement of the plunger can dispense the bone cement. The system can also include a pressure release system, which can be coupled to the housing and can be movable to release pressure within the dispenser housing without moving the plunger.

18 Claims, 8 Drawing Sheets

(56) References Cited

U.S. PATENT DOCUMENTS

| | | | |
|---|---|---|---|
| 984,037 A * | 2/1911 | Sheets | 604/125 |
| 3,052,239 A * | 9/1962 | Silver et al. | 604/89 |
| 3,164,303 A * | 1/1965 | Trautmann | 222/190 |
| 3,281,023 A | 10/1966 | Bruck et al. | |
| 3,417,971 A | 12/1968 | Blank et al. | |
| 3,749,084 A * | 7/1973 | Cucchiara | 600/575 |
| 4,312,343 A | 1/1982 | LeVeen et al. | |
| 4,338,925 A | 7/1982 | Miller et al. | |
| 4,476,866 A * | 10/1984 | Chin | 606/194 |
| 4,583,974 A | 4/1986 | Kokernak | |
| 4,654,027 A * | 3/1987 | Dragan et al. | 604/99.03 |
| 4,723,938 A | 2/1988 | Goodin et al. | |
| 4,832,692 A | 5/1989 | Box et al. | |
| 5,071,040 A | 12/1991 | Laptewicz, Jr. | |
| 5,599,312 A * | 2/1997 | Higashikawa | 604/191 |
| 5,603,701 A * | 2/1997 | Fischer | 604/211 |
| 5,630,800 A * | 5/1997 | Blank et al. | 604/82 |
| 5,704,918 A * | 1/1998 | Higashikawa | 604/191 |
| 5,842,785 A | 12/1998 | Brown et al. | |
| 5,842,786 A | 12/1998 | Solomon | |
| 5,876,116 A | 3/1999 | Barker et al. | |
| 5,961,211 A | 10/1999 | Barker et al. | |
| 6,019,765 A | 2/2000 | Thornhill et al. | |
| 6,024,480 A | 2/2000 | Seaton et al. | |
| 6,033,105 A | 3/2000 | Barker et al. | |
| 6,367,962 B1 | 4/2002 | Mizutani et al. | |
| 6,383,190 B1 | 5/2002 | Preissman | |
| 6,550,957 B2 | 4/2003 | Mizutani et al. | |
| 6,699,214 B2 | 3/2004 | Gellman | |
| 7,014,640 B2 | 3/2006 | Kemppainen et al. | |
| 7,134,782 B2 | 11/2006 | Coffeen et al. | |
| 7,270,667 B2 | 9/2007 | Faccioli et al. | |
| 7,306,611 B2 * | 12/2007 | Cirotteau et al. | 606/92 |
| 7,371,241 B2 | 5/2008 | Evans et al. | |
| 2002/0013553 A1 | 1/2002 | Pajunk et al. | |
| 2003/0065333 A1* | 4/2003 | DeMayo | 606/92 |
| 2005/0105385 A1* | 5/2005 | McGill et al. | 366/139 |
| 2005/0124997 A1 | 6/2005 | Pajunk et al. | |
| 2007/0060924 A1 | 3/2007 | Choi | |
| 2008/0105707 A1* | 5/2008 | Girgis et al. | 222/144 |
| 2010/0121310 A1* | 5/2010 | Simonton et al. | 604/518 |

* cited by examiner

METHOD AND APPARATUS FOR DELIVERING BONE CEMENT

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, cements, etc., to secure the damaged tissue.

For example, in the case of damaged bone tissue, bone cement can be surgically inserted around the damaged bone tissue to facilitate the healing of the bone tissue. In one example, bone cement can be inserted into fractured vertebrae to stabilize the damaged bone tissue. The present teachings provide one or more surgical instruments for repairing damaged tissue, such as in the case of a compression fracture in a vertebrae.

A bone cement system is provided. The system can include a housing, which can define at least a throughbore. The throughbore can extend from a proximal end of the housing to a distal end of the housing. The system can also include a dispenser housing received in the throughbore of the housing that is adapted to receive a bone cement. The system can include a plunger, which can be releasably coupled to the proximal end of the housing and can be received into the dispenser housing so that movement of the plunger relative to the dispenser housing dispenses the bone cement from the distal end of the housing. The system can also include a pressure release system, which can be coupled to the housing and can be movable to release pressure within the dispenser housing without moving the plunger.

Further provided is a bone cement system. The system can include a housing, which can define at least a throughbore. The throughbore can extend from a proximal end of the housing to a distal end of the housing. The system can also include a dispenser housing received in the throughbore of the housing that is adapted to receive a bone cement. The system can include a plunger releasably coupled to the proximal end of the housing and received into the dispenser housing so that a distalmost end of the plunger is adjacent to the bone cement to enable the plunger to push the bone cement out of the distal end of the housing. The plunger can have a proximal end, a distal end and a throughbore defined from the proximal end to the distal end. The system can include a pressure release system, which can be received within the throughbore of the plunger and can be rotatable relative to the plunger to allow bone cement to flow behind the distalmost end of the plunger to release pressure within the dispenser housing.

Also provided is a method of using the above described system that comprises inserting the bone cement into the dispenser housing, and positioning a cannulated access needle into a desired position in an anatomy. The method can also include coupling a tubing member between the cannulated access needle and the distal end of the housing, and advancing the plunger within the dispenser housing to push the bone cement out of the distal end of the housing, through the tubing member and into the cannulated access member. The method can include moving the pressure release system relative to the housing to release the pressure acting on the dispenser housing without moving the plunger.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

DESCRIPTION OF VARIOUS ASPECTS

The following description is merely exemplary in nature and is not intended to limit the present teachings, application, or uses. It should be understood that throughout the drawings, corresponding reference numerals indicate like or corresponding parts and features. Although the following description is related generally to a system and method for use in an anatomy to repair damaged tissue, such as in a compression fracture in a spine, it will be understood that the system and method as described and claimed herein, can be used in any appropriate surgical procedure, such as in securing an implant to an anatomy. Further, the present orthopedic fixation teachings are applicable to both primary and reconstruction procedures. Therefore, it will be understood that the following discussions are not intended to limit the scope of the present teachings and claims herein.

Figure 1:
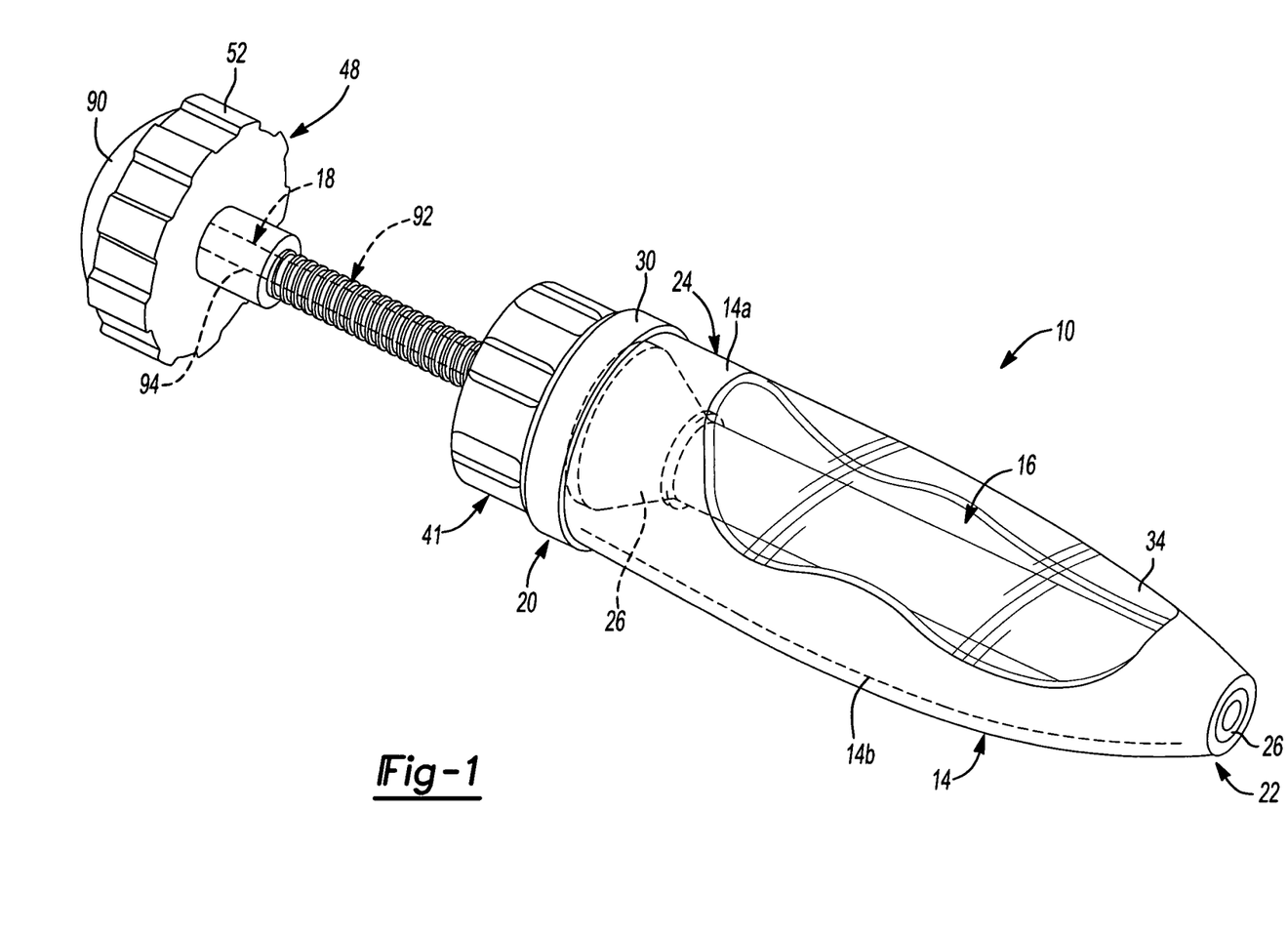
FIG. 1 is a schematic illustration of an exemplary method and apparatus for delivering bone cement according to the present teachings.
Figure 2:
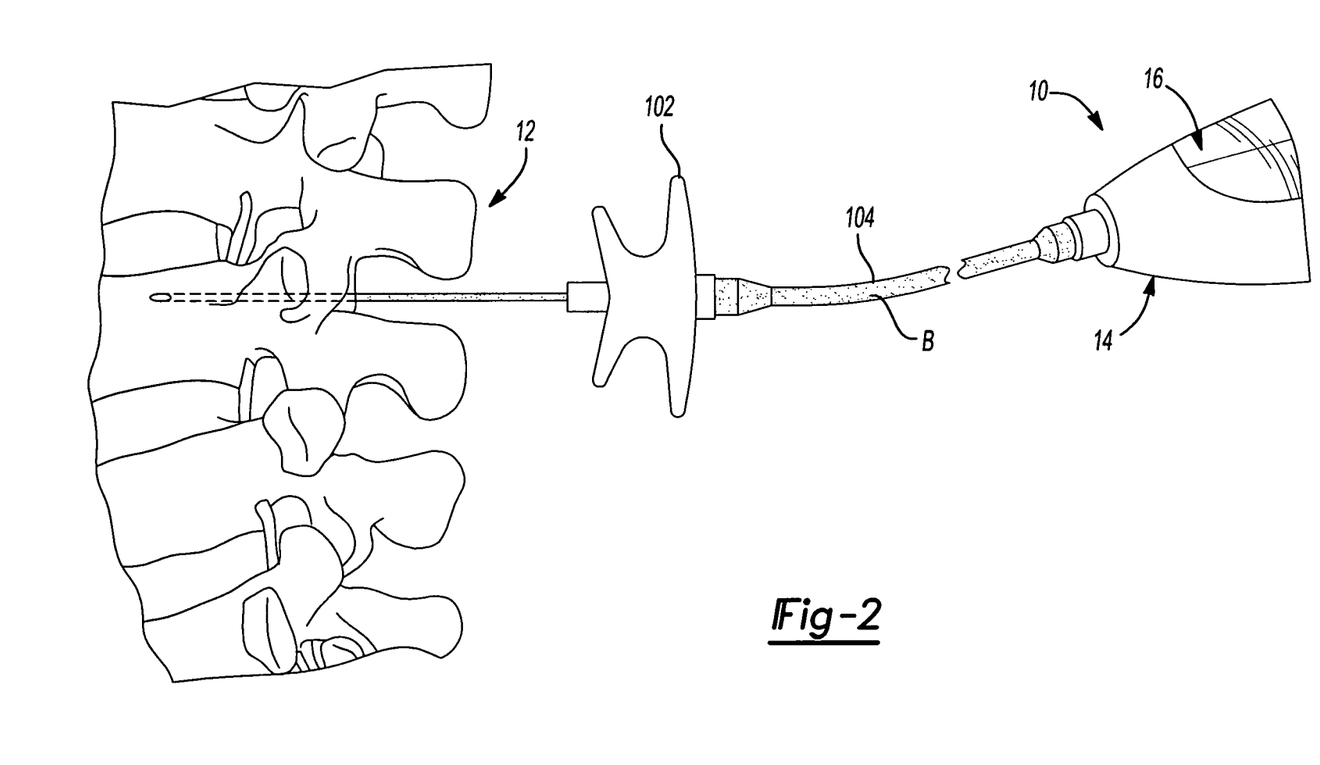
FIG. 2 is a schematic environmental illustration of the apparatus of FIG. 1 repairing an anatomy, such as a vertebral fracture, according to the present teachings.
Figure 3:
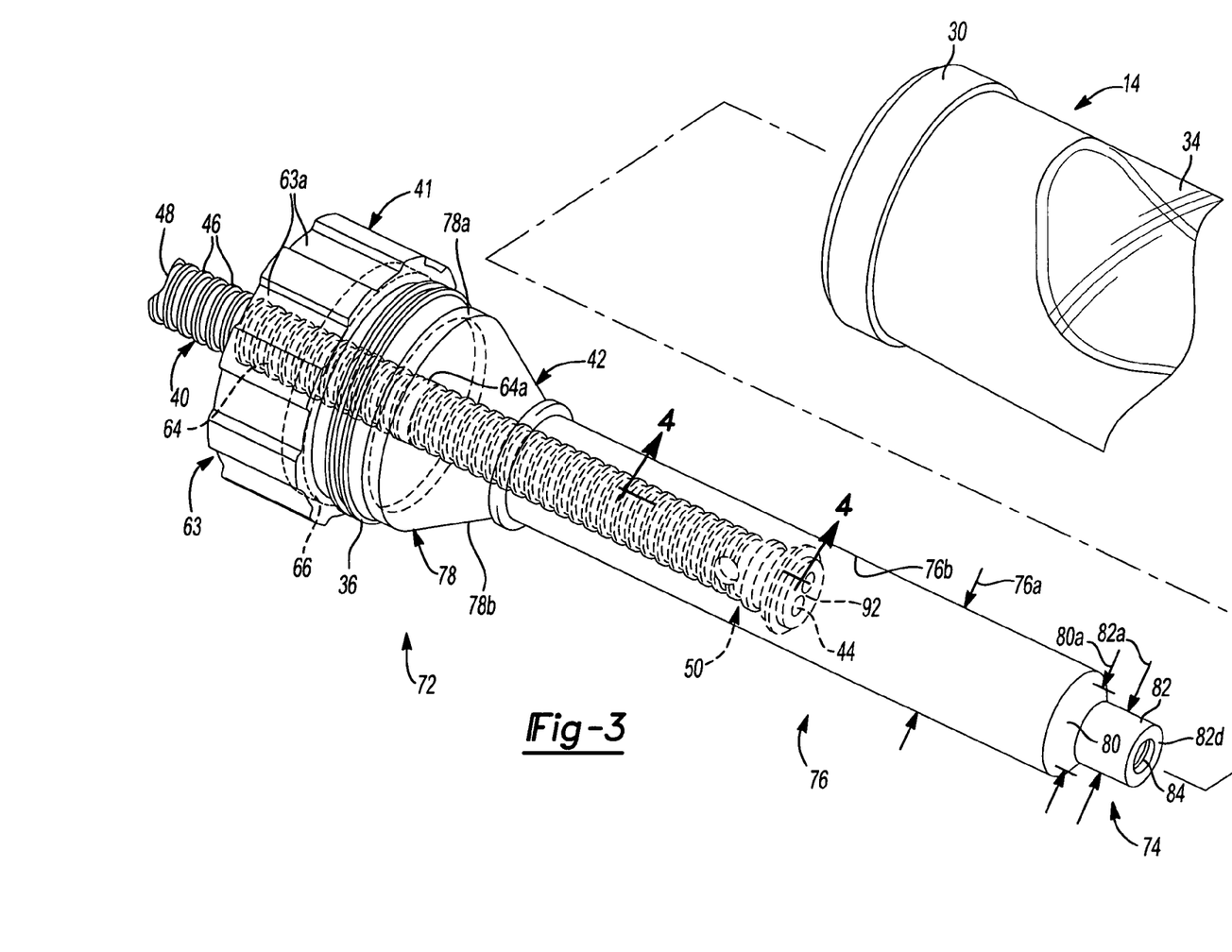
FIG. 3 is an exploded schematic illustration of the apparatus of FIG. 1.
Figure 4:
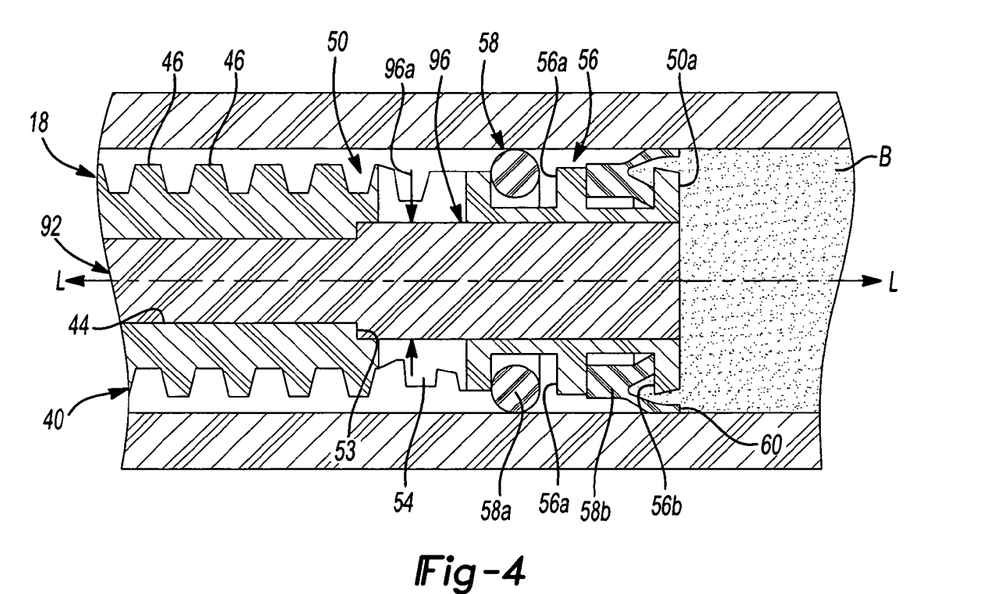
FIG. 4 is a schematic cross-sectional illustration of the apparatus of FIG. 1, taken along line 4-4 of FIG. 3, in which a pressure release system associated with the apparatus of FIG. 1 is in a first position.
Figure 5:
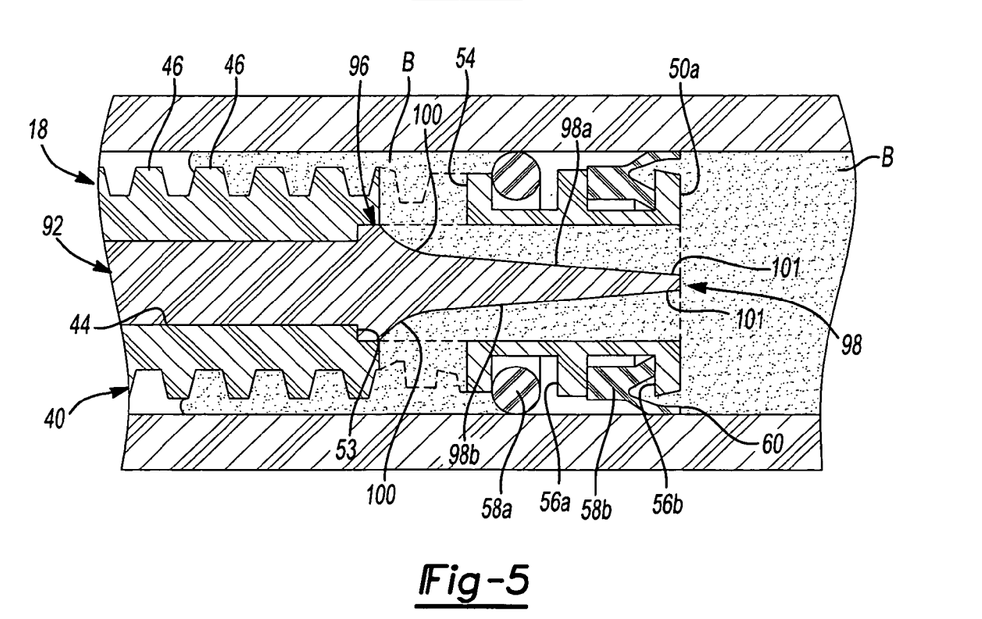
FIG. 5 is a schematic cross-sectional illustration of the apparatus of FIG. 1, taken along line 4-4 of FIG. 3, in which a pressure release system associated with the apparatus of FIG. 1 is in a second position.

With reference to FIGS. 1-6, a bone cement system 10 for delivering bone cement is shown. The bone cement system 10 can be used to repair damaged tissue in an anatomy, such as a compression fracture between adjacent vertebrae 12 (FIG. 2). The bone cement system 10 can include a housing 14, a dispenser system 16 and a pressure release system 18 (FIGS. 3-5). The dispenser system 16 can cooperate with the housing 14 to enable the selective dispensing of pressurized bone cement B (FIG. 2) from the housing 14, and the pressure release system 18 can be used to relieve excess pressure within the housing 14 (FIG. 5).

With reference to FIG. 1, the housing 14 can include a proximal end 20, a distal end 22 and one or more walls 24, which can couple the proximal end 20 to the distal end 22. In one example, the housing 14 can comprise a clam-shell type housing, in which a first member 14a can be snap-fit with a second member 14b, however, the housing 14 could be integrally formed or molded if desired. Generally, the housing 14 can define a throughbore 26, which can receive the dispenser system 16 and the pressurized bone cement B, as will be discussed. The throughbore 26 can generally be tapered, such that at the proximal end 20, a first diameter of the throughbore 26 can be larger than a second diameter of the throughbore 26 at the distal end 22.

The proximal end 20 can include a grip 30. The grip 30 can be formed adjacent to the proximal end 20, and in one example, can be formed about the sidewall 24. The grip 30 can provide a surface for the user to grasp during the use of the bone cement system 10. The distal end 22, as will be discussed, can be coupled to various surgical instruments to enable the bone cement B to enter the selected portion of the anatomy.

The wall 24 can couple the proximal end 20 to the distal end 22, and can define the throughbore 26. The wall 24 can generally taper from the distal end 22 to the proximal end 20, and can define a window 34. The window 34 can enable the user to view the bone cement B within the housing 14, and generally, can enable the user to view the bone cement B within the dispenser system 16.

The dispenser system 16 can include a mating portion 36, a plunger 40, a cap 41 and a dispenser housing 42. The mating portion 36 can couple the plunger 40 to the dispenser housing 42. In one example, the mating portion 36 can comprise a plurality of threads formed about the dispenser housing 42, however, the mating portion 36 can comprise any suitable mechanism, such as mechanical fasteners, an adhesive, a keyed portion, etc. The mating portion 36 can also be formed to enable the bone cement system 10 to be coupled to a suitable bone cement mixing device, such as the Optipac® V Bone Cement Mixing System commercially available from Biomet, Inc. of Warsaw, Ind.

With reference to FIG. 3, the plunger 40 can be controlled by an operator to dispense the bone cement B from the dispenser housing 42, which can be disposed within the housing 14. The plunger 40 can be cannulated, and thus, can include a throughbore 44. The throughbore 44 can generally be sized to receive at least a portion of the pressure release system 18, as will be discussed in greater detail herein. An exterior surface of the plunger 40 can include at least one or a plurality of threads 46, which can enable the plunger 40 to move relative to the dispenser housing 42 and the housing 14, as will be discussed. The plunger 40 can include a proximal end 48 (FIG. 1) and a distal end 50 (FIG. 3).

With reference to FIG. 1, the proximal end 48 can include a graspable portion 52. The graspable portion 52 can be fixed to the proximal end 48, so that the surgeon can rotate the graspable portion 52 to rotate the plunger 40. In one example, the graspable portion 52 can be formed on or molded on the proximal end 48, but the graspable portion 52 could also be fixed to the proximal end 48 via any suitable mechanism, such as mechanical fasteners, bonding, etc.

With reference to FIGS. 4 and 5, the distal end 50 can include a countersink 53, a cross bore 54, one or more grooves 56 and one or more sealing members 58. In addition, in one example, the throughbore 44 can have a larger diameter at the distal end 50, as defined by the countersink 53, to enable the receipt of the pressure release system 18, as will be discussed herein. The countersink 53 can be defined adjacent to the cross bore 54, and can be defined about the throughbore 44. Generally, the countersink 53 can cooperate with at least a portion of the pressure release system 18 to ensure that the pressure release system 18 remains properly positioned within the throughbore 44 of the plunger 40, as will be discussed.

The cross bore 54 can be formed to be about perpendicular to a longitudinal axis L of the plunger 40, and can generally be formed to intersect the throughbore 44. The cross bore 54 can cooperate with the pressure release system 18, as will be discussed herein. The cross bore 54 can be formed behind or adjacent to the one or more grooves 56, away from a distal-most end 50a.

The one or more grooves 56, in one example, can include a first groove 56a and a second groove 56b. The first groove 56a and the second groove 56b can be about equal in size, but it should be understood that the first groove 56a and second groove 56b can have any suitable size to receive the one or more sealing members 58. Generally, the first groove 56a and the second groove 56b can be formed about a circumference of the plunger 40, with a depth sufficient enough to receive the one or more sealing members 58.

The one or more sealing members 58, in one example, can include a first sealing member 58a and a second sealing member 58b. The first sealing member 58a can be received in the first groove 56a, and the second sealing member 58b can be received in the second groove 56b. Generally, the first sealing member 58a and the second sealing member 58b can be sized to seal against the dispenser housing 42 to maintain the pressure of the bone cement B. The first sealing member 58a, in one example, can comprise an annular ring, such as an O-ring, and can have a width sized to enable the first sealing member 58a to move, slide or translate within the first groove 56a. The second sealing member 58b, in one example, can comprise an annular ring having a conical flange 60. The conical flange 60 can extend outwardly from the annular ring of the second sealing member 58b, and can cooperate with the dispenser housing 42 and the distalmost end 50a of the plunger 40 to push the bone cement B out of the dispenser housing 42.

With reference to FIGS. 1 and 3, the dispenser system 16 can include the cap 41. The cap 41 can be sized to mate with the mating portion 36 of the dispenser housing 36, and can include a grip surface 63, a throughbore 64 and a second mating portion 66. The grip surface 63 can facilitate the assembly of the plunger 40 to the housing 14, as will be discussed. In one example, the grip surface 63 can include one or more formed recesses 63a, which the operator can grasp.

The throughbore 64 can be defined through a center of the cap 41, and can be sized to receive at least a portion of the plunger 40 therethrough. In one example, the throughbore 64 can include threads 64a, which can mate with the threads 46 of the plunger 40 to enable the plunger 40 to advance in the dispenser housing 42 and pressurize the bone cement B. The throughbore 64 can generally be formed in the cap 41 such that a centerline of the throughbore 64 is coaxially aligned with a centerline of the dispenser housing 42.

With reference to FIG. 3, the second mating portion 66 can be formed adjacent to the grip surface 63. The second mating portion 66 can couple the cap 41 to the housing 14. In this regard, the second mating portion 66 can cooperate with the mating portion 36 of the dispenser housing 42 to securely, but releasably couple the plunger 40 to the housing 14. In one example, the second mating portion 66 can comprise a plurality of threads, which can cooperate with the mating portion 36, however, the second mating portion 66 and the mating portion 36 can comprise any suitable releasable coupling mechanism, such as a press-fit, friction fit, keyed coupling mechanism, etc. Further, the second mating portion 66 could comprise a plurality of threaded apertures, and the mating portion 36 could comprise a plurality of threaded apertures for receipt of a plurality of threaded fasteners, etc. In addition, the plunger 40 could be fixedly coupled to the dispenser housing 42, via an adhesive bond, for example, if desired.

The dispenser housing 42 can receive the bone cement B from a suitable source, such as an OptiVac® bone cement mixing system manufactured by Biomet, Inc. of Warsaw, Ind. With reference to FIG. 3, the dispenser housing 42 can be sized to fit within the housing 14, and generally, the dispenser housing 42 can be retained in a snap-fit fashion within the housing 14 by the clamshell nature of the housing 14. The dispenser housing 42 can include a proximal end 72 and a distal end 74, which can be coupled together via a tubular body 76.

The proximal end 72 can include the mating portion 36, which can couple the plunger 40 to the dispenser housing 42. The proximal end 72 can also include a transition portion 78. The transition portion 78 of the proximal end 72 can transition the proximal end 72 to the tubular body 76. In this regard, the transition portion 78 can include a first end 78a and a second end 78b. The transition portion 78 can generally taper from the first end 78a to the second end 78b. The first end 78a can be held adjacent to the second mating portion 66, and can have a diameter that can be larger than the second end 78b, which can be coupled to the tubular body 76. In one example, the transition portion 78 can be conical in shape, however, the transition portion 78 can have any desired shape, so long as at least a portion of the plunger 40 can pass through the transition portion 78.

The distal end 74 can include a tapered section 80 and a nozzle 82, which can be formed to define a throughbore 84. The tapered section 80 can transition the tubular body 76 into the nozzle 82. In addition, the tapered section 80 can act as a stop for the plunger 40. In this regard, the tapered section 80 can have at least one diameter 80a, which can be sized such that the plunger 40 cannot advance into the throughbore 84.

The nozzle 82 can be coupled adjacent to the tapered section 80, and can have a diameter 82a, which can be smaller than the diameter 80a of the tapered section 80. The smaller diameter 82a of the nozzle 82 can facilitate the pressurized release of bone cement B from the housing 14. Generally, the nozzle 82 can be sized such that a distalmost end 82d of the nozzle 82 can be substantially aligned with a distalmost end 14a of the housing 14 to enable bone cement B to exit the bone cement system 10 via the nozzle 82.

The tubular body 76 can extend between the proximal end 72 and the distal end 74. The tubular body 76 can define a throughbore 86, which can be coaxially aligned with the throughbore 84 of the distal end 74. The tubular body 76 can generally have a uniform diameter 76a, which can be sized to enable the plunger 40 to move within the tubular body 76. In one example, the diameter 76a of the tubular body 76 can be such that the conical flange 60 of the second sealing member 58b can contact an interior surface 76b of the tubular body 76 to keep the bone cement B about the distalmost end 50a of the plunger 40. In addition, the diameter 76a can be sized such that bone cement B released by the pressure release system 18 can be received within the tubular body 76, adjacent to the plunger 40 (FIG. 5).

In this regard, with reference to FIGS. 1 and 3-5, the pressure release system 18 can be used by the operator to relieve excess pressure in the bone cement system 10 by providing at least one passage for the release of some of the pressurized bone cement B from the distalmost end 50a of the plunger 40. In one example, the pressure release system 18 can comprise a graspable member 90 (FIG. 1) and a body 92 (FIGS. 3-5). The graspable member 90 can be coupled to a proximal end 94 of the body 92, and can enable the user to manipulate or rotate the body 92. In one example, the graspable member 90 can comprise an annular cap. If desired, the graspable member 90 can include one or more indicia, which can provide a visual cue for the operator regarding the use of the body 92.

With reference to FIGS. 4 and 5, the body 92 can be sized to be received into the throughbore 44 defined in the plunger 40. The body 92 can include the proximal end 94 and a distal end 96. The distal end 96 can have a diameter 96a, which can be larger than a diameter 92a of the body 92. The diameter 96a of the distal end 96 can cooperate with the countersink 53 of the plunger 40 and the increased diameter of the throughbore 44 at the distal end 50 of the plunger 40 to ensure that the distal end 96 of the body 92 remains adjacent to or within the distal end 50 of the plunger 40.

With reference to FIG. 5, the distal end 96 of the body 92 can also include at least one or a plurality of slots 98. In one example, the body 92 can include a first slot 98a and a second slot 98b. The first slot 98a can be formed opposite the second slot 98b, or can be formed about 180 degrees from the second slot 98b. Generally, as illustrated in FIG. 5, the slots 98 can taper from a first end 100 to a second end 101 to form a gentle slope. The slots 98 can enable the bone cement B to flow behind the distalmost end 50a of the plunger 40 to relieve pressure from in front of the distalmost end 50a of the plunger 40.

In this regard, with reference to FIG. 5, the slots 98 can be rotated into alignment with the cross bore 54, which can enable bone cement B to flow along the slots 98, through the cross bore 54 and into the tubular body 76 at an area defined behind the sealing members 58. The flowing of at least a portion of the bone cement B from the distalmost end 50a of the plunger 40 can reduce a portion of the pressure acting on the distalmost end 50a of the plunger 40. This can be desirable in certain instances, as too much pressure may reduce the precision of the dispensing of the bone cement B. When it is not desirable to release pressure in the bone cement system 10, the slots 98 can be rotated out of alignment with the cross bore 54 (FIG. 4), thereby preventing the release or flowing of the bone cement B beyond the distalmost end 50a of the plunger 40.

In order to assemble the bone cement system 10, the dispenser housing 42 can be coupled to the housing 14 via the snap-fit engagement between the housing 14 and the dispenser housing 42. The plunger 40 can be coupled to the housing 14 via the engagement between the cap 41 and the dispenser housing 42, after the receipt of the mixed bone cement B.

In this regard, the bone cement mixing system, such as the OptiVac® bone cement mixing system manufactured by Biomet, Inc. of Warsaw, Ind., can be coupled to the mating portion 36 of the dispenser housing 42. The bone cement B can then be inserted into the dispenser housing 42. Then, the plunger 40 can be inserted into the dispenser housing 42, by coupling the cap 41 to the dispenser housing 42. The pressure release system 18 can generally be coupled to the plunger 40 prior to coupling the plunger 40 with the dispenser housing 42. Thus, when the plunger 40 is coupled to the dispenser housing 42, the bone cement system 10 can be ready for use with the anatomy.

Figure 6:
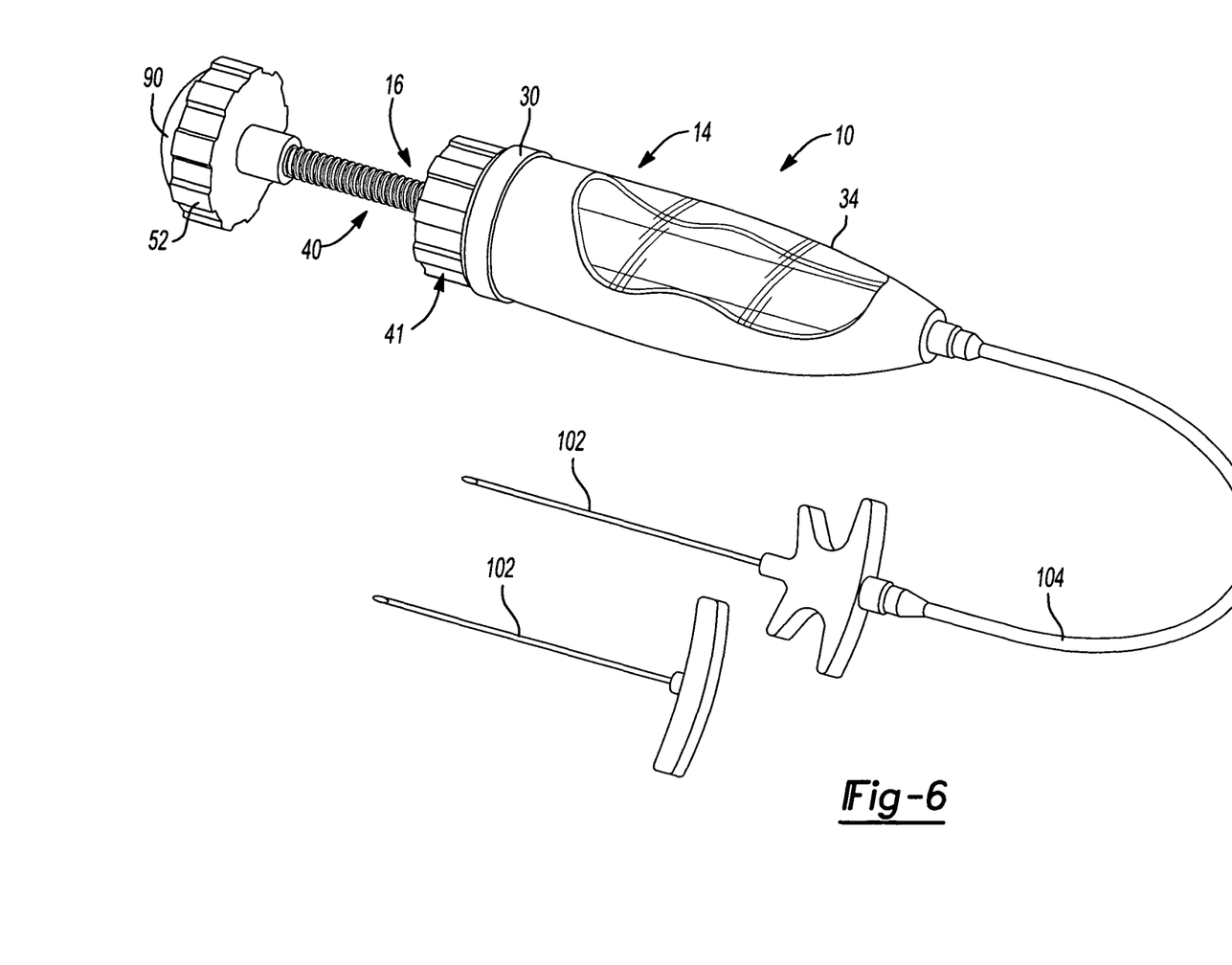
FIG. 6 is a schematic environmental illustration of an exemplary kit that includes the apparatus of FIG. 1 according to the present teachings.

In one example, with reference to FIGS. 2 and 6, one or more cannulated access needles 102 and flexible tubing member 104 can be used with the bone cement system 10 to dispense the bone cement B to a desired location in the anatomy. With reference to FIG. 2, a desired one of the access needles 102 can be positioned at the desired location in the anatomy, and the flexible tubing member 104 can couple the bone cement system 10 to the cannulated throughbore in the access needle 102. Thus, in this example, one end of the flexible tubing member 104 can be coupled to or inserted into the nozzle 82 of the distal end 74 and another end of the flexible tubing member 104 can be coupled to the cannulated access needle 102.

With reference to FIGS. 2 and 6, with the bone cement system 10 coupled to the cannulated access needle 102, the user can begin to rotate the plunger 40 via the graspable portion 52 to advance the plunger 40 within the dispenser housing 42. The plunger 40 can be advanced in the dispenser housing 42 until the distalmost end 50a of the plunger 40 contacts the tapered section 80 of the distal end 65 of the dispenser housing 42, or until the user has delivered a desired quantity of bone cement B.

If, during the dispensing of the bone cement B, the pressure acting on the distalmost end 50a of the plunger 40 is too high as determined by the user, with reference to FIGS. 4 and 5, the user can rotate the pressure release system 18 so that the slots 98 are aligned with the cross bore 54 of the plunger 40. Generally, in one example, the pressure release system 18 can be rotated 90 degrees in either direction via the graspable member 90 to align the slots 98 with the cross bore 54 (FIG. 5). The alignment of the slots 98 with the cross bore 54 can enable the bone cement B to flow behind the sealing members 58 to relieve the pressure acting on the distalmost end 50a. Once the user has determined that enough pressure has been relieved, the user can rotate the pressure release system 18 such that the slots 98 are no longer aligned with the cross bore 54 (FIG. 4). In one example, the pressure release system 18 can be rotated another 90 degrees to move the slots 98 out of alignment with the cross bore 54. Thus, the bone cement system 10 can enable the user to dispense bone cement B at a desired pressure, which can be controlled via the pressure release system 18.

Figure 7:
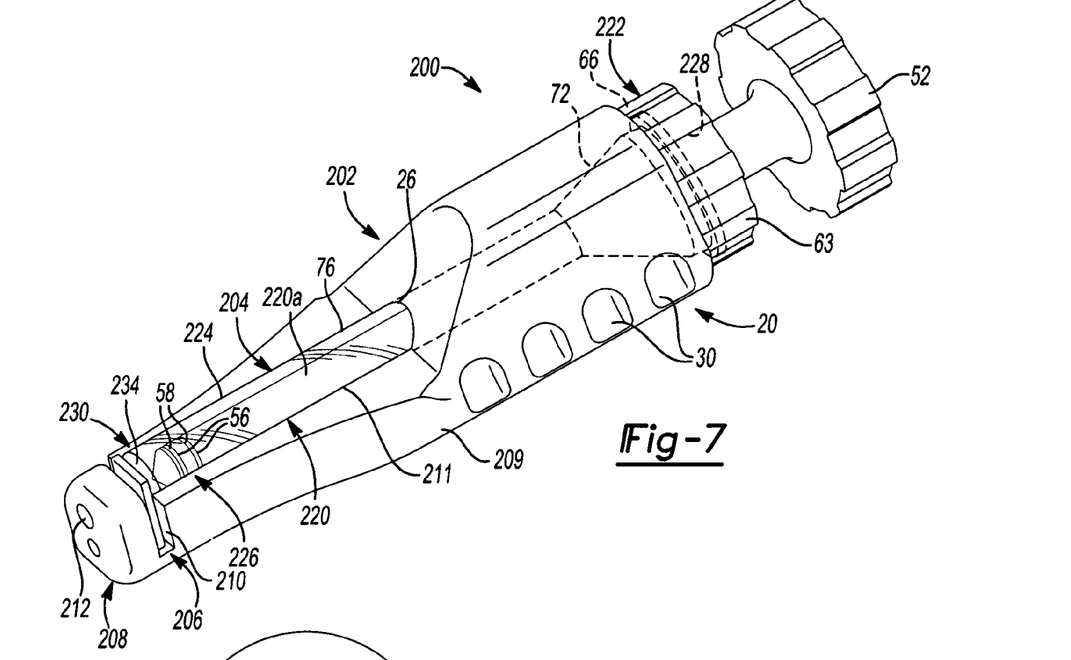
FIG. 7 is a schematic illustration of one of various embodiments for the method and apparatus for delivering bone cement, according to various teachings.
Figures 8, 9:
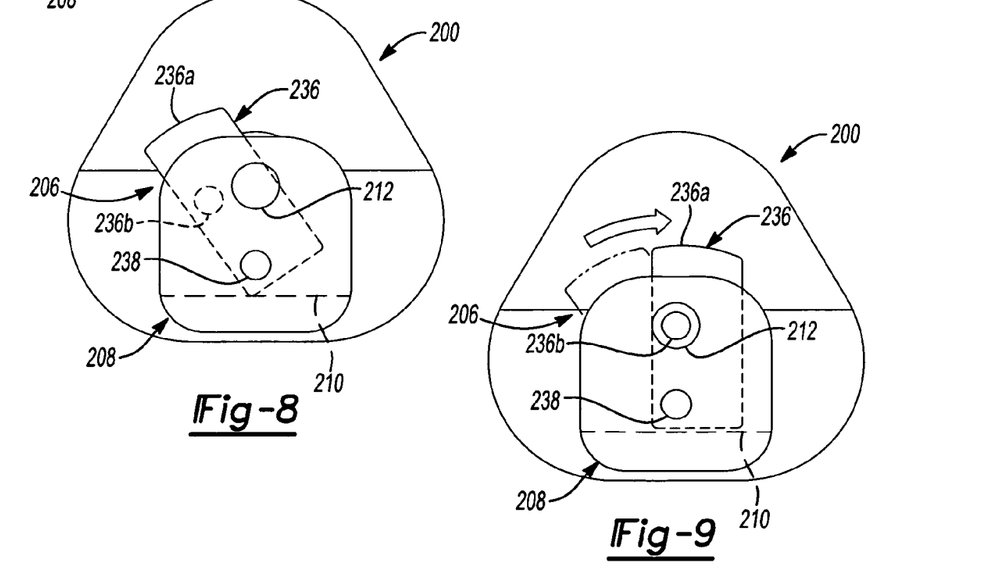
FIG. 8 is a schematic end view of the apparatus of FIG. 7, in which a cut-off system associated with the apparatus is in a first position.
FIG. 9 is a schematic end view of the apparatus of FIG. 7, in which a cut-off system associated with the apparatus is in a second position.

With reference now to FIGS. 7-9, in one example, a bone cement system 200 can be employed to deliver bone cement B to an anatomy. As the bone cement system 200 can be similar to the bone cement system 10 described with reference to FIGS. 1-6, only the differences between the bone cement system 10 and the bone cement system 200 will be discussed in great detail herein, and the same reference numerals will be used to denote the same or similar components.

The bone cement system 200 can include a housing 202, a dispenser system 204 and a pressure release system or cut-off system 206. The dispenser system 204 can cooperate with the housing 202 to enable the selective dispensing of pressurized bone cement B from the housing 202, and the cut-off system 206 can be used to stop the flow of bone cement B from the housing 202.

The housing 202 can include the proximal end 20, a distal end 208 and a wall 209, which can couple the proximal end 20 to the distal end 208. Generally, the housing 202 can define the throughbore 26, which can receive the dispenser system 204 and the pressurized bone cement B. The proximal end 20 of the housing 202 can include the mating portion 28 and the grip 30. The distal end 208 can include a slot 210 and a nozzle 212.

The slot 210 can be formed through the distal end 208 of the housing 202, and can generally be formed substantially perpendicular to the throughbore 26. The slot 210 can be sized to receive the cut-off system 206, as will be discussed herein. The slot 210 can be positioned adjacent to the nozzle 212. The nozzle 212 can be in communication with the dispenser system 16 to receive the pressurized bone cement B. The nozzle 212 can be coupled to various surgical instruments, such as the access needle 102, if desired, to enable the bone cement B to be dispensed from the housing 202 into a selected portion of the anatomy.

The wall 209 can couple the proximal end 20 to the distal end 208, and can surround and at least partially enclose the throughbore 26. The wall 209 can taper from the proximal end 20 to the distal end 208, and can generally define an opening 211 through which at least a portion of the throughbore 26 and at least a portion of the dispenser system 204 can be visible. Thus, the opening 211 can enable the user to view the bone cement B within the dispenser system 204.

The dispenser system 204 can include a plunger 220, the cap 222 and the dispenser housing 224. The plunger 220 can be controlled by an operator to dispense the bone cement B from the dispenser housing 224, which can be disposed within the housing 202. An exterior surface 220a of the plunger 220 can be generally smooth, but can include at least one or a plurality of threads, if desired, to assist in the advancement of the plunger 220. Generally, the plunger 220 can move or slide within the dispenser housing 224 to advance the bone cement B through the nozzle 212.

The plunger 220 can also include the proximal end 48 and a distal end 226. The proximal end 48 can include the graspable portion 52, which can allow the surgeon to control the advancement of the plunger 220 within the dispenser housing 224. The distal end 226 can include the one or more grooves 56 and the one or more sealing members 58. As discussed previously herein, the first sealing member 58a can be received in the first groove 56a, and the second sealing member 58b can be received in the second groove 56b. Generally, the first sealing member 58a and the second sealing member 58b can be sized to seal against the dispenser housing 42 to maintain the pressure of the bone cement B.

The cap 222 can be sized to mate with the housing 202, and can include the grip surface 63, a throughbore 228 and the second mating portion 66. The throughbore 228 can be defined through a center of the cap 222, and can be sized to receive the plunger 220 therethrough. In one example, the throughbore 228, can have a generally smooth surface to enable the plunger 220 to slidably pass therethrough, but it should be understood that the throughbore 228 could include threads, which could mate with threads formed on the plunger 220, if desired. The throughbore 228 can generally be formed in the cap 222 such that a centerline of the throughbore 228 is coaxially aligned with a centerline of the dispenser housing 224. The second mating portion 66 can couple the cap 222 to the housing 202. In this regard, the second mating portion 66 can cooperate with the mating portion 28 of the housing 202 to securely, but releasably couple the plunger 220 to the housing 202, as discussed previously with regard to the cap 41 and housing 14.

The dispenser housing 224 can be sized to fit within the housing 14, and generally, the dispenser housing 224 can be retained within the housing 202 via a snap-fit. The dispenser housing 224 can receive the bone cement B from a suitable source, such as an OptiVac® bone cement mixing system manufactured by Biomet, Inc. of Warsaw, Ind. The dispenser housing 224 can include the proximal end 72 and a distal end 230, which can be coupled together via the tubular body 76.

The proximal end 72 can couple the dispenser housing 224 to the housing 202, via the engagement of the clam-shell housing 202 about the transition portion 78. The proximal end 72 can also include the mating portion 36. The distal end 230 can define a throughbore 234. The diameter of the throughbore 234 can be substantially smaller than the diameter of the tubular body 76, to transition the dispenser housing 224 into the nozzle 212. The tubular body 76 can be sized to cooperate with the sealing members 58 of the plunger 220 to assist the plunger 220 in pushing the bone cement B out of the dispenser housing 224 and into the nozzle 212 when the cut-off system 206 is in the first, opened position (FIG. 9).

With reference to FIGS. 8 and 9, the cut-off system 206 can be used to control the flow of the bone cement B out of the nozzle 212. In this regard, the cut-off system 206 can be operable in a first, opened position (FIG. 9) to enable the bone cement B to flow out of the nozzle 212, and can be operable in a second, closed position (FIG. 8) to prevent the flow of the bone cement B out of the nozzle 212. The cut-off system 206 can include a member 236 and a pivot 238.

The member 236 can be received within the slot 210, and can generally be movable, rotatable or pivotable about the pivot 238. Generally, the member 236 can be rectangular, and at least a portion 236a of the member 236 can extend beyond the housing 202 to enable the surgeon to manually move the member 236 about the pivot 238. The member 236 can also define a bore 236b, which can enable the bone cement B to flow through the member 236, into the nozzle 212, when the cut-off system 206 is in the first, opened position (FIG. 9). The member 236 can include a throughbore that can receive the pivot 238, or the pivot 238 could be integrally formed with the member 236, if desired. Generally, the pivot 238 can define a pivot point or pivot axis for the member 236, which can enable the member 236 to be moved between the first, opened position and the second, closed position. In one example, the pivot 238 can comprise a post or arm or pin, which can be coupled to or pass through the member 236 and at least a portion of the housing 202 to enable the member 236 to move relative to the housing 202, via the pivot 238.

In this regard, the member 236 can be movable to enable or prevent the flow of bone cement B through the nozzle 212. Thus, when the bone cement system 200 is assembled, such that the dispenser housing 224 is received in the housing 202 and the member 236 is coupled to the housing 202 via the pivot 238, the bone cement B can be received into the dispenser housing 224. In one example, the bone cement B can be received from a suitable bone cement mixing device, such as the OptiVac® bone cement mixing system manufactured by Biomet, Inc. of Warsaw, Ind.

Generally, with reference to FIGS. 7-9, the bone cement mixing system can be coupled to the mating portion 36 of the dispenser housing 224, and then, the bone cement B can be inserted into the dispenser housing 224. After the bone cement mixing system is uncoupled from the dispenser housing 224, the plunger 220 can be inserted into the dispenser housing 224, by coupling the cap 222 to the housing 202. Then, the operator can move the member 236 from the second, closed position to the first, opened position, and can depress the plunger 220 to dispense bone cement B out of the nozzle 212. As discussed with regard to the bone cement system 10, the nozzle 212 can be coupled to various surgical instruments to dispense the bone cement B into these various instruments, such as the tubing member 104 and a cannulated needle 102, however, the nozzle 212 could be positioned such that the nozzle 212 can advance bone cement B directly into the anatomy.

Figure 10:
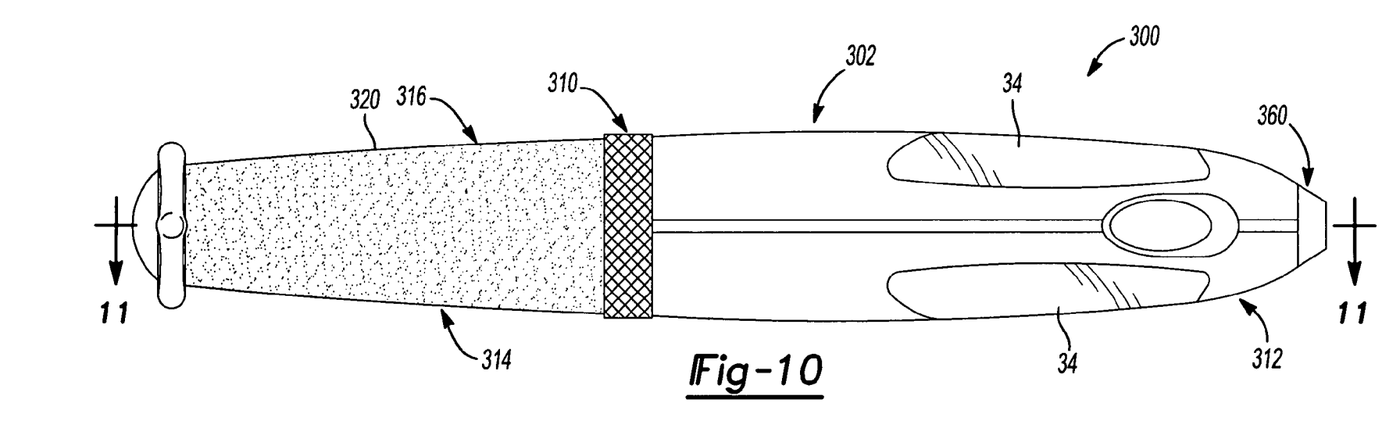
FIG. 10 is a schematic illustration of one of various embodiments for the method and apparatus for delivering bone cement, according to various teachings.
Figure 11:
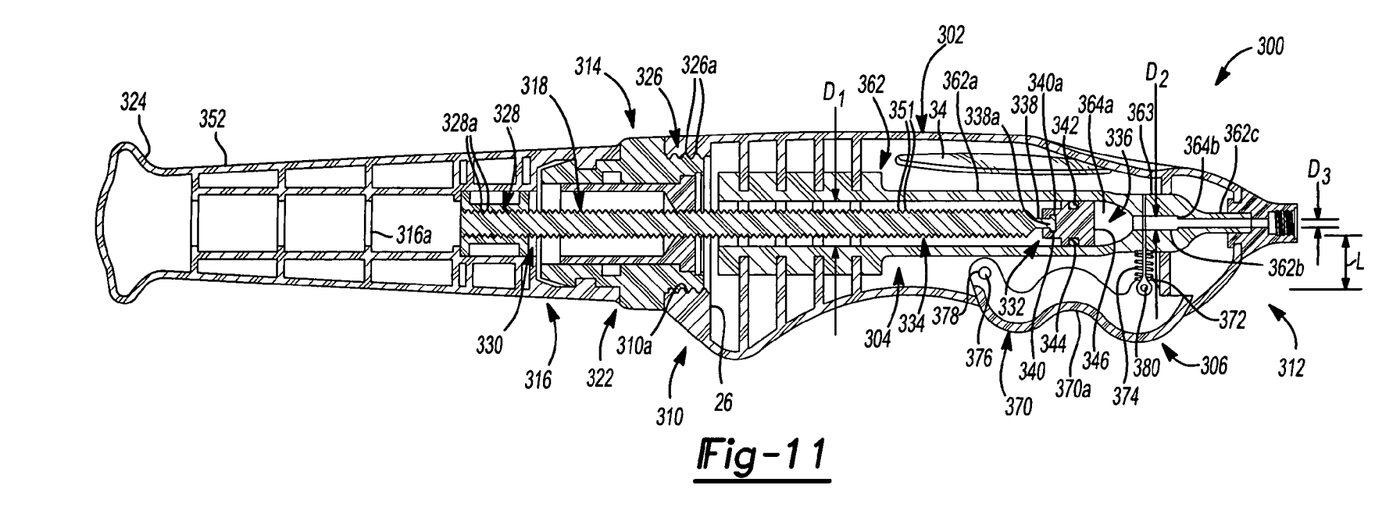
FIG. 11 is a schematic cross-sectional illustration of the apparatus of FIG. 10, taken along line 11-11 of FIG. 10.

With reference now to FIGS. 10 and 11, in one of various examples, a bone cement system 300 can be employed to deliver bone cement B to an anatomy. As the bone cement system 300 can be similar to the bone cement system 10 described with reference to FIGS. 1-6 and the bone cement system 200 described with reference to FIGS. 7-9, only the differences between the bone cement system 10, the bone cement system 200 and the bone cement system 300 will be discussed in great detail herein, and the same reference numerals will be used to denote the same or similar components.

With reference to FIGS. 10 and 11, the bone cement system 300 can include a housing 302, a dispenser system 304 (FIG. 11) and a cut-off or pressure release system 306 (FIG. 11). The dispenser system 304 can cooperate with the housing 302 to enable the selective dispensing of pressurized bone cement B from the housing 302, and the pressure release system 306 can be used to reduce the pressure of the bone cement B exiting the housing 302, in one example, by stopping the flow of bone cement B.

With reference to FIGS. 10-11, the housing 302 can include a proximal end 310 and a distal end 312, which can cooperate to define the throughbore 26 through the housing 302. Generally, the housing 302 can define the throughbore 26, which can receive the dispenser system 304 and the pressurized bone cement B. The proximal end 310 of the housing 302 can include a mating portion 310a, and a plunger grip system 314. The mating portion 310a can couple the plunger grip system 314 to the housing 302. In one example, the mating portion 310a can comprise a plurality of threads, however, the mating portion 310a can comprise any mechanism capable of coupling the plunger grip system 314 to the housing 302.

The plunger grip system 314 can include a plunger housing 316, a plunger 318 (FIG. 11) and a grip 320 (FIG. 10). Generally, the plunger housing 316 can define a throughbore 316a, and the plunger 318 can be slidably or rotatably received within the throughbore 316a. The grip 320 can enable the operator to easily manipulate the plunger housing 316.

With reference to FIG. 11, the plunger housing 316 can be generally cylindrical, and can define a slight taper from a first end 322 to a second end 324 to facilitate an operator grasping the plunger housing 316. The first end 322 of the plunger housing 316 can include a second mating portion 326 and a plunger engagement feature 328. The second mating portion 326 can comprise threads 326a, which can engage the mating portion 310a of the housing 302 to couple the plunger grip system 314 to the housing 302. It should be noted, however, that the second mating portion 326 can comprise any suitable feature that can releasably couple the plunger housing 316 to the housing 302, such as a snap-fit, press-fit, mechanical fastener, etc.

The plunger engagement feature 328 can enable the plunger 318 to be advanced from the plunger housing 316. In one example, the plunger engagement feature 328 can comprise at least one or a plurality of threads 328a formed about a circumference of a throughbore 316a, which can engage the plunger 318 such that the rotation of the plunger housing 316 can move the plunger 318 relative to the plunger housing 316.

It should be understood, however, that any suitable mechanism could be used to move the plunger 318 relative to the plunger housing 316, such as a power source in communication with the plunger 318, etc. and further that the plunger engagement feature 328 could be coupled to or formed on an exterior surface of the plunger housing 316, if desired.

The plunger 318 can be received within and movable relative to the plunger housing 316. The plunger 318 can include a proximal end 330 and a distal end 332, which can be coupled together via a plunger body 334. The proximal end 330 can be retained within the second end 324 of the plunger housing 316. The distal end 332 can include a plunger head 336, which can be coupled to the plunger body 334 via a post 338 formed at the distal end 332. The plunger head 336 can include a retainer 340, a groove 342, a sealing member 344 and a face 346.

The retainer 340 can receive the post 338 from the proximal end 330, and in one example, the retainer 340 can define at least a slot 340a, which can receive a portion of the post 338, such as a lip 338a formed on the post 338. Generally, the retainer 340 can cooperate with the post 338 to enable the plunger 318 to translate or slide within the throughbore 26 as the plunger 318 is rotated within the throughbore 26. The groove 342 can be formed adjacent to the face 346, and can be sized to receive the sealing member 344. The face 346 can push the bone cement B out of the housing 302, with the aid of the sealing member 344.

The plunger body 334 can be configured to enable the plunger 318 to move within the plunger housing 316. In one example, the plunger body 334 can include a plurality of threads 351, which can matingly engage the threads 328a of the plunger housing 316. The engagement of the threads 351 with the threads 328a can allow an operator to advance the plunger 318 through the dispenser system 304.

With reference to FIGS. 10 and 11, the grip 320 can be formed on an external surface 352 (FIG. 11) of the plunger housing 316. In one example, the grip 320 can be overmolded onto the external surface 352 of the plunger housing 316, however, the grip 320 could be adhesively bonded to a portion of the external surface 352. The grip 320 can facilitate the operator's engagement with the plunger grip system 314.

With reference to FIGS. 10 and 11, the distal end 312 of the housing 302 can include at least one window 34 and a nozzle 360. The window 34 can enable the operator to view the bone cement B within the dispenser system 304. With reference to FIG. 11, the nozzle 360 can be tapered, and can direct the pressurized bone cement B out of the housing 302. In one example, as discussed with regard to the bone cement system 10, the nozzle 360 can be coupled to various surgical instruments to dispense the bone cement B into these various instruments, such as the tubing member 104 and a cannulated needle 102, however, the nozzle 360 could be positioned such that the nozzle 360 can advance bone cement B directly into the anatomy. The nozzle 360 can be in communication with the dispenser system 304 to receive the bone cement B.

With reference to FIG. 11, the dispenser system 304 can be sized to fit within the housing 302, and generally, the dispenser system 304 can be retained in a snap-fit fashion within the housing 302 by the clamshell nature of the housing 302. The dispenser system 304 can receive the bone cement B from a suitable source, such as an OptiVac® bone cement mixing system manufactured by Biomet, Inc. of Warsaw, Ind. The dispenser system 304 can define one or more tubular housing sections 362 for receipt of the bone cement B. In one example, the dispenser system 304 can include a first tubular section 362a, a second tubular section 362b and a third tubular section 362c.

The first tubular section 362a can have a diameter D1, which can be larger than a diameter D2 of the second tubular section 362b. The first tubular section 362a can be positioned near the mating portion 28 of the housing 302. The first tubular section 362a can define a tapered section 364a, which can transition the first tubular section 362a to the second tubular section 362b. The second tubular section 362b can also define a tapered section 364b, which can transition the second tubular section 362b into the third tubular section 362c. The second tubular section 362b can define a slot 363, which can receive at least a portion of the pressure release system 306 therein. The third tubular section 362c can have a diameter D3, which can be smaller than the diameter D2 of the second tubular section 362b. The third tubular section 362c can be positioned adjacent to and in communication with the nozzle 360. The progressive reduction in the diameters D1-D3 from the first tubular section 362a to the third tubular section 362c can further pressurize the bone cement B, as the bone cement B is pushed towards the nozzle 360 by the plunger 318.

With continuing reference to FIG. 11, the pressure release system 306 can be coupled to the distal end 312 of the housing 302. The pressure release system 306 can stop the flow of the bone cement B, and thus, can reduce the pressure of the bone cement B exiting the nozzle 360. In one example, the pressure release system 306 can include a trigger 370, a biasing member or spring 372 and a blade 374.

The trigger 370 can be coupled to the distal end 312 of the housing 302 by a post 376 formed on the housing 302. The trigger 370 can comprise any suitable shape that can enable the operator to easily manipulate and depress the trigger 370. In one example, the trigger 370 can include a concave depression 370a, which can be sized to receive the operator's finger. The trigger 370 can also include a pivot axis or bore 378, which can be received on the post 376 such that the trigger 370 can rotate or pivot about the post 376 relative to the housing 302. Typically, the pivot bore 378 can be positioned on an end of the trigger 370, which is opposite a coupling post 380. The coupling post 380 can couple the spring 372 to the trigger 370, and can couple the blade 374 to the trigger 370.

The spring 372 can be coupled at one end to the trigger 370 at the coupling post 380. The other end of the spring 372 can bias against the second tubular section 362b, adjacent to the slot 363. The spring 372 can provide a force against the depression of the trigger 370 so that the trigger 370 can be generally biased in a first position. Thus, in order to depress the trigger 370 or move the trigger 370 into a second position, the operator can overcome the force of the spring 372. Once the operator releases the trigger 370, the force of the spring 372 can move the trigger 370 back into the first position. The depression of the trigger 370 or movement of the trigger 370 into the second position can move the blade 374 from a first position to a second position.

In this regard, the blade 374 can be coupled at an end to the coupling bore 380. Generally, the blade 374 can have a length L, which can enable the blade 374 to be retained within a portion of the slot 363 when the trigger 370 is in a first position, and enables the blade 374 to extend through the slot 363 to block the flow of bone cement B through the second tubular section 362b when the trigger 370 is in the second position. In this regard, the trigger 370, when depressed by the operator, can move the blade 374 to cut-off or block the flow of bone cement through the dispenser system 304, which can reduce the pressure of the bone cement B exiting the nozzle 360.

With the dispenser system 304 retained within the distal end 312 of the housing 302, and the pressure release system 306 coupled to the distal end 312 of the housing 302, a bone cement mixing system can be coupled to the mating portion 310a of the housing 302. As discussed, the bone cement mixing system can comprise any suitable bone cement mixing system, such as the OptiVac® bone cement mixing system manufactured by Biomet, Inc. of Warsaw, Ind. The bone cement B can be received into the tubular sections 362 of the dispenser system 304. The bone cement mixing system can be removed from the housing 302, and then, the plunger grip system 314 can be coupled to the mating portion 310a of the housing 302 via the second mating portion 326.

The operator can rotate the plunger housing 316 using the grip 320 to advance the plunger 318 into the dispenser system 304. The advancement of the plunger 318 can push the bone cement B into and out of the nozzle 360. If, during the dispensing of the bone cement B, the pressure of the bone cement B becomes to high, or if the operator wishes to stop or cut-off the flow of the bone cement B, the operator can depress the trigger 370. The movement of the trigger 370 from the first position to the second, depressed position can cause the blade 374 to block or cut-off the flow of bone cement B through the dispenser system 304.

Accordingly, the bone cement systems 10, 200, 300 described herein can enable an operator to dispense bone cement B at a desired pressure, which can be controlled via the pressure release system 18, 306 or cut-off system 206. The controlled release of the bone cement B can provide the operator with flexibility in the dispensing of the bone cement B, which can enable the bone cement B to be used in a variety of applications. In addition, by enabling a suitable bone cement mixing system to be releasably coupled to the bone cement systems 10, 200, 300, the operator can easily fill the bone cement systems 10, 200, 300 with little mess or contact with the actual bone cement B.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

Figure 12:
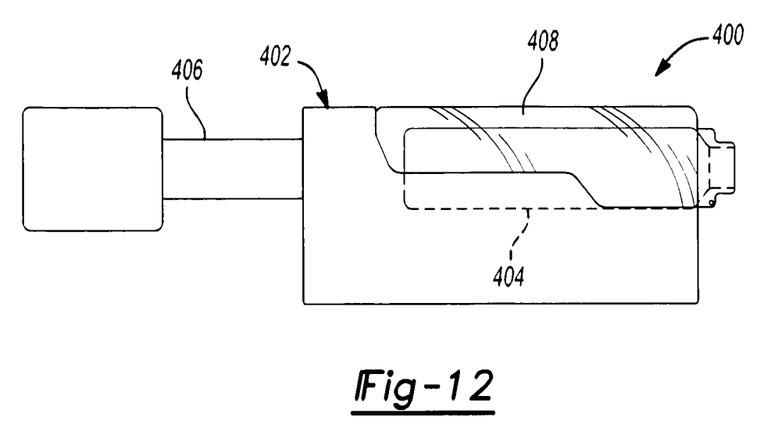
FIG. 12 is a schematic illustration of one of various embodiments for the method and apparatus for delivering bone cement, according to various teachings, with a housing associated with the apparatus in a first position.
Figure 13:
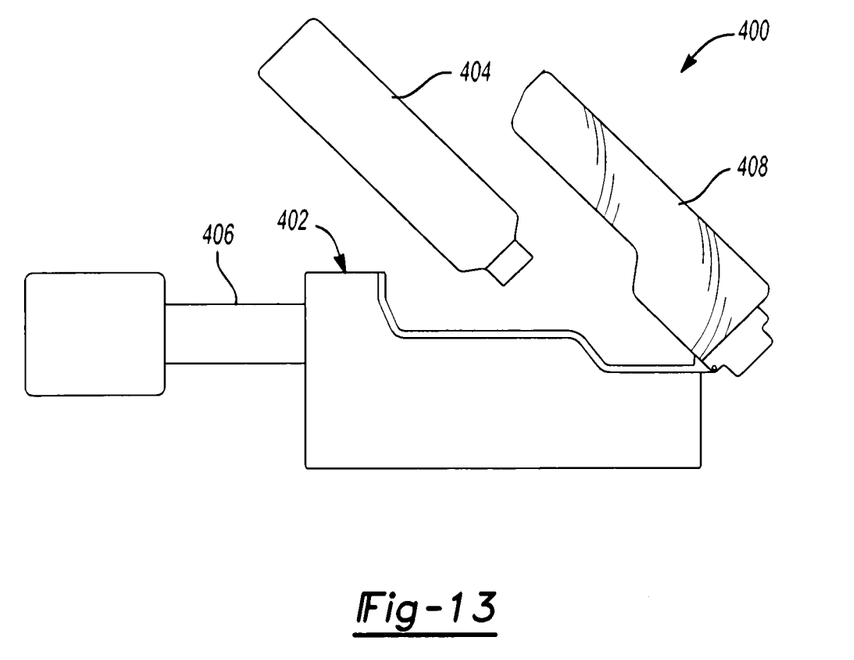
FIG. 13 is a schematic illustration of one of various embodiments for the method and apparatus for delivering bone cement, according to various teachings, with a housing associated with the apparatus in a second position.

For example, while the dispenser system 16, 204, 304 has been described herein as being secured within the housing 14, 202, 304 for receiving the bone cement B from a suitable bone cement mixing system, those of skill in the art will appreciate that the present disclosure, in its broadest aspects, may be constructed somewhat differently. In this regard, with reference to FIGS. 12 and 13, a bone cement system 400 can include a housing 402, a dispenser system 404 and a plunger 406, which can move relative to the housing 402. The housing 402 can be reusable, and can include a rotatable window 408, which can be moved between an opened position (FIG. 13) and a closed position (FIG. 12) to receive the dispenser system 404. The dispenser system 404 can generally be pre-filled with the bone cement B, and can generally be employed for one-time use. Once the dispenser system 404 is placed and secured within the housing 402, the plunger 406 can be advanced to push the bone cement B out of the dispenser system 404, and out of the housing 402. Once a desired amount of bone cement B has been dispensed from the housing 402, or once the dispenser system 404 is emptied, the window 408 can be moved from the closed position (FIG. 12) to the opened position (FIG. 13), and the dispenser system 404 can be removed from the housing 402. The housing 402 is then ready to receive a new pre-filled dispenser system 404.

What is claimed is:

1. A bone cement system comprising:
a housing that defines at least a throughbore that extends from a proximal end of the housing to a distal end of the housing;
a dispenser housing received in the throughbore of the housing that is adapted to receive a bone cement;
a plunger releasably coupled to the proximal end of the housing and received into the dispenser housing so that movement of the plunger relative to the dispenser housing dispenses the bone cement from the distal end of the housing, the plunger having a proximal end, a distal end, a throughbore extending from the proximal end of the plunger to the distal end of the plunger, and a cross bore directly communicating with the throughbore of the plunger and extending in a radial direction completely through the plunger; and
a pressure release system that is coupled to the housing and that is movable relative to the plunger to release pressure within the dispenser housing, the pressure release system including a body received in the throughbore of the plunger, the body having a distal end that is rotatable within the throughbore of the plunger relative to the cross bore of the plunger between a first position and a second position, without translating the body relative to the plunger along a longitudinal axis of the plunger extending from the proximal end of the plunger to the distal end of the plunger, such that in the first position the distal end of the body blocks the cross bore to prevent bone cement from passing through the cross bore and in the second position the distal end of the body allows bone cement to pass through the cross bore and flow proximately behind a distalmost end of the plunger to relieve pressure at the distalmost end of the plunger, wherein the throughbore of the plunger includes a counterbore disposed at the distal end of the plunger and having an increased diameter relative to the remainder of the throughbore, and the distal end of the body has an increased diameter relative to the remainder of the body such that the distal end of the body forms a shoulder which the counterbore engages to prevent translation of the body along the longitudinal axis of the plunger.

2. The system of claim 1, wherein the distal end of the body defines at least one slot.

3. The system of claim 2, wherein the body is rotatable via a proximal end of the body relative to the plunger so that the at least one slot is aligned with the cross bore.

4. The system of claim 2, wherein the at least one slot includes two slots each formed on opposite sides of the distal end of the body.

5. The system of claim 1, wherein the cross bore is formed about perpendicular to the longitudinal axis of the plunger.

6. The system of claim 1, further comprising:
a cannulated access needle that is insertable into an anatomy to a desired site; and a tubing member coupled to the cannulated access needle and to the distal end of the housing to enable the bone cement to flow from the distal end of the housing into the anatomy.

7. A bone cement system comprising:
a housing that defines at least a throughbore that extends from a proximal end of the housing to a distal end of the housing;
a dispenser housing received in the throughbore of the housing that is adapted to receive a bone cement;
a plunger releasably coupled to the proximal end of the housing and received into the dispenser housing so that a distalmost end of the plunger is adjacent to the bone cement to enable the plunger to push the bone cement out of the distal end of the housing, the plunger having a proximal end, a distal end, a longitudinal throughbore extending from the proximal end of the plunger to the distal end of the plunger, and a cross bore radially extending from the throughbore and completely through the plunger; and
a pressure release system received within the throughbore of the plunger and including a body having a distal end that is rotatable within the throughbore of the plunger relative to the cross bore of the plunger, without translating the body relative to the plunger along a longitudinal axis of the plunger extending from the proximal end of the plunger to the distal end of the plunger to block and open the cross bore of the plunger, so as to respectively prevent the bone cement from flowing through the cross bore and to allow bone cement to flow through the cross bore and behind the distalmost end of the plunger to release pressure within the dispenser housing, wherein the throughbore of the plunger includes a counterbore disposed at the distal end of the plunger and having an increased diameter relative to the remainder of the throughbore, and the distal end of the body has an increased diameter relative to the remainder of the body such that the distal end of the body forms a shoulder which the counterbore engages to prevent translation of the body along the longitudinal axis of the plunger.

8. The system of claim 7, wherein the plunger is releasably coupled to the housing by a cap that defines a throughbore, the throughbore defining a plurality of threads that engage a plurality of threads formed about a body of the plunger to enable the plunger to be rotatably advanced into the dispenser housing.

9. The system of claim 7, wherein the bone cement flows into an area defined between the plunger and the dispenser housing.

10. The system of claim 9, wherein the body has a proximal end that includes a graspable portion, and at least one slot defined in the distal end, which can be aligned with the cross bore to enable the bone cement to flow behind the distalmost end of the plunger.

11. The system of claim 10, wherein the cross bore is formed about perpendicular to the throughbore of the plunger.

12. The bone cement system of claim 1, wherein the body is coupled to the housing such that the body is movable relative to the plunger to release pressure within the dispenser housing without moving the plunger relative to the dispenser housing.

13. The bone cement system of claim 1, wherein the throughbore of the plunger is open at the distalmost end of the plunger to receive cement in an axial direction when the body is in the second position.

14. The bone cement system of claim 10, wherein the cross bore is blocked by the distal end of the body when the body is in a first position, and the throughbore of the plunger is open at the distalmost end to receive cement in an axial direction when the body is in a second position.

15. The bone cement system of claim 1 wherein the throughbore of the plunger extends along the longitudinal axis of the plunger from the proximal end of the plunger to the distal end of the plunger.

16. The bone cement system of claim 7 wherein the distal end of the body of the pressure release system is rotatable within the throughbore relative to the cross bore of the plunger between a first position and a second position, without translating the body along the longitudinal axis of the plunger, such that in the first position the distal end of the body blocks the cross bore to prevent bone cement from passing through the cross bore and in the second position the distal end of the body allows bone cement to pass through the cross bore and flow proximately behind the distalmost end of the plunger to relieve pressure at the distalmost end of the plunger.

17. A bone cement system comprising:
a dispenser housing adapted to receive bone cement;
a plunger releasably received within the dispenser housing and configured to push the bone cement through a distal end of the dispenser housing, the plunger having a proximal end, a distal end, a longitudinal throughbore extending from the proximal end of the plunger to the distal end of the plunger, and a cross bore in communication with the throughbore and extending radially from the through bore and completely through the plunger; and
a pressure release system received within the throughbore of the plunger and including a body defining slots, wherein the body is rotatable within the throughbore of the plunger, between a first position and a second position, relative to the cross bore of the plunger to align the slots with the cross bore without translating the pressure release system relative to the plunger along a longitudinal axis of the plunger extending from the proximal end of the plunger to the distal end of the plunger, such that in the first position a distal end of the body blocks the cross bore to prevent bone cement from passing through the cross bore and in the second position the distal end of the body allows bone cement to pass through the cross bore and flow proximately behind a distalmost end of the plunger to relieve pressure at the distalmost end of the plunger; and wherein the throughbore of the plunger includes a counterbore disposed at the distal end of the plunger and having an increased diameter relative to the remainder of the throughbore, and the distal end of the body has an increased diameter relative to the remainder of the body such that the distal end of the body forms a shoulder which the counterbore engages to prevent translation of the body along the longitudinal axis of the plunger.

18. The bone cement system of claim 17 wherein the counterbore engages the distal end of the body to position the body along the longitudinal axis of the plunger such that the distal end of the body is disposed within the distal end of the plunger.

* * * * *